United States Patent [19]

Drach

[11] Patent Number: 4,652,258
[45] Date of Patent: Mar. 24, 1987

[54] CATHETER WITH EXPANSIBLE CONNECTOR AND METHOD

[75] Inventor: George W. Drach, Tucson, Ariz.

[73] Assignee: The Kendall Company, Boston, Mass.

[21] Appl. No.: 683,051

[22] Filed: Dec. 18, 1984

[51] Int. Cl.[4] .................................. A61M 31/00
[52] U.S. Cl. .................................. 604/53; 604/96; 604/283
[58] Field of Search .................................. 604/49–55, 604/99, 100, 101, 103–105, 171, 280, 283; 128/4, 7, 343, 348.1

[56] References Cited

U.S. PATENT DOCUMENTS

| 2,541,691 | 6/1949 | Eicher | 128/343 |
|---|---|---|---|
| 3,042,045 | 7/1962 | Sheridan | 604/283 |
| 3,144,020 | 9/1964 | Zingale | 128/4 |
| 3,503,399 | 3/1970 | Ettman | 604/100 |
| 3,565,078 | 2/1971 | Valliancourt | 604/283 |
| 3,599,641 | 8/1971 | Sheridan | 604/283 |
| 3,811,449 | 5/1974 | Gravlee | 128/343 |
| 3,884,242 | 5/1975 | Bazelle | 604/103 |
| 4,211,234 | 6/1980 | Fischer | 128/343 |
| 4,315,509 | 2/1982 | Smit | 128/348 |
| 4,405,314 | 10/1983 | Cope | 604/51 |
| 4,464,175 | 8/1984 | Altman et al. | 604/99 |

Primary Examiner—John D. Yasko
Attorney, Agent, or Firm—Powell L. Sprunger

[57] ABSTRACT

A catheter comprising, an elongated shaft having a drainage lumen, and an expansive hollow connector extending from a proximal end of the shaft, and defining a continuation of the drainage lumen.

6 Claims, 7 Drawing Figures

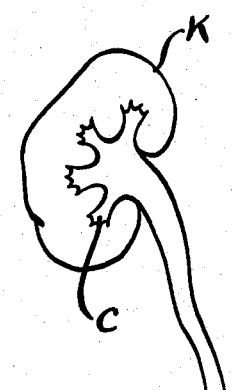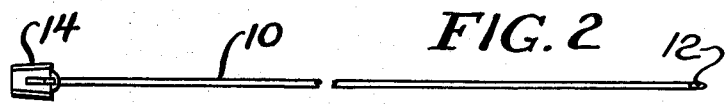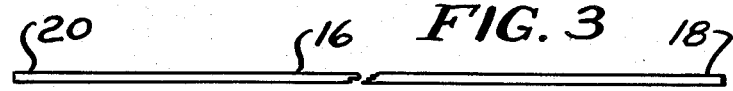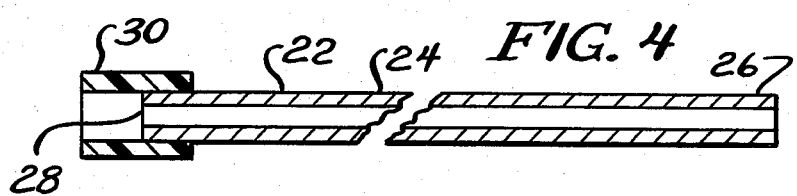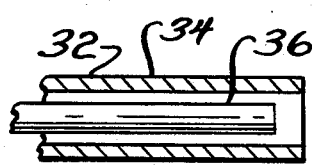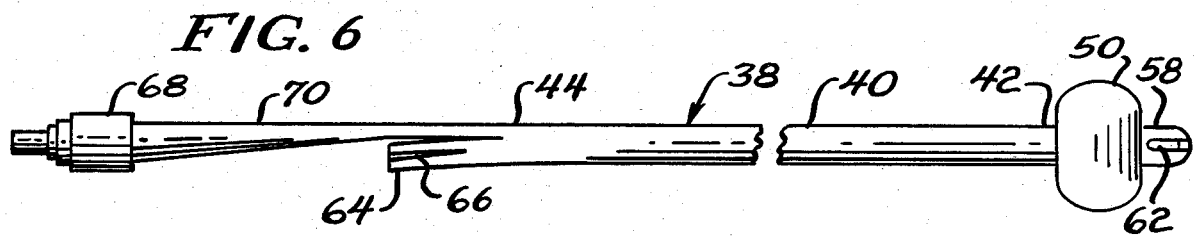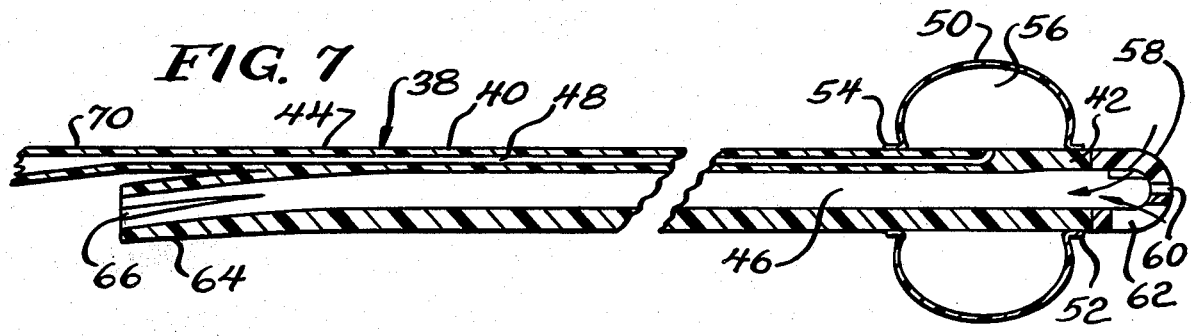

CATHETER WITH EXPANSIBLE CONNECTOR AND METHOD

BACKGROUND OF THE INVENTION

The present invention relates to catheters.

When the ureter or kidney of a patient is obstructed by a stone, it is necessary to stabilize the kidney through drainage because an increase of pressure in the kidney could result in loss of the kidney. Such a procedure is called a nephrostomy procedure. First, a small gauge hollow needle is passed under radiologic vision until a tip of the needle is located in the renal calyces to obtain access to the kidney chamber. With the needle in place, a flexible elongated guide wire is passed through the needle, and the needle is removed with the guide wire in place to establish a path to the kidney. Next, a plurality of dilators are inserted over the guide wire in order to increase the size of the path to the kidney, and the dilators are then removed. In the past, a catheter is then placed over the guide wire, with the catheter having a pig tail which is located in the kidney. Although nephrostomy has been completed in this manner, it is desired to improve the procedure.

SUMMARY OF THE INVENTION

A principal feature of the present invention is the provision of an improved catheter for performing a nephrostomy procedure.

The catheter of the invention comprises, an elongated shaft having a drainage lumen, and a hollow connector extending from a proximal end of the shaft, and defining a continuation of the drainage lumen.

A feature of the present invention is that the connector is expansible for connection to a drainage tube.

Another feature of the invention is that the connector has outer transverse dimensions approximately less than the outer diameter of the shaft.

Still another feature of the invention is that the catheter has an inflation valve located proximal the connector.

Still another feature of the invention is that the connector has outer transverse dimensions approximately less than the outer diameter of the shaft.

Another feature of the invention is that the sheath of a scope may be passed over the valve, connector, and shaft of the catheter.

Yet another feature of the invention is the provision of a method of performing a nephrostomy procedure.

Further features will become more fully apparent in the following description of the embodiments of this invention and from the appended claims.

DESCRIPTION OF THE DRAWINGS

In the drawings:

FIG. 1 is a diagrammatic view of a kidney of a patient;

FIG. 2 is a fragmentary elevational view of a needle for use in a nephrostomy procedure;

FIG. 3 is a fragmentary elevational view of a guide wire for use in the procedure;

FIG. 4 is a fragmentary elevational view of a stylet for use in the procedure;

FIG. 5 is a fragmentary elevational view of a scope for use in the procedure;

FIG. 6 is a fragmentary elevational view of a catheter of the present invention; and FIG. 7 is a fragmentary sectional view of the catheter of FIG. 6.

DESCRIPTION OF THE PREFERRED EMBODIMENTS

Referring now to FIG. 1, there is shown a kidney K of a patient having a renal calyces C to form a cavity in the kidney K.

Referring to FIG. 2, there is shown a hollow needle 10 having a sharp distal tip 12 and a proximal hub 14. Referring to FIG. 3, there is shown a guide wire 16 of flexible material having a distal end 18 and a proximal end 20. Referring to FIG. 4, there is shown a stylet 22 having an elongated rigid tube 24. The tube 24 has a distal end 26 and a proximal end 28. As shown, a hollow tubular section 30 of flexible plastic material is frictionally secured to an outer surface of the proximal end 28. Referring to FIG. 5, there is shown a scope 32 having an outer hollow sheath 34, and an inner optic telescope 36 removably received within the sheath 34.

The catheter 38 of the present invention is illustrated in FIGS. 6 and 7. The catheter 38 has an elongated elastic shaft 40 having a distal end 42 and a proximal end 44. The shaft 40 also has a drainage lumen 46 extending therethrough. The shaft 40 has an inflation lumen 48 extending through a wall of the shaft to the proximal end 44 of the shaft 40. The catheter 38 also has an elastic sleeve 50 bonded to a distal portion of the shaft 40 in circumferential zones 52 and 54, such that the sleeve 50 defines a cavity 56 beneath the sleeve 50 communicating with the inflation lumen 48.

The catheter 38 has a formed tip 58 bonded to the distal end 42 of the shaft 40. The tip 58 has an opening 60 extending through a distal end of the tip 58 and communicating with the drainage lumen 46. The tip 58 also has a plurality of drainage eyes 62 located proximal the opening 60 and extending through the tip 58 and communicating with the drainage lumen 46.

The catheter 38 has an expansible hollow connector 64 extending from the proximal end 44 of the shaft 40, such that the connector 64 defines a continuation of the drainage lumen 46. The connector 64 has a plurality of longitudinally extending flutes 66 to permit expansion of the connector 64 to receive an adaptor of a drainage tube. In its unexpanded form, the connector 64 has outer dimensions approximately less than the outer diameter of the shaft 40.

The catheter 38 has a narrow inflation valve 68 located proximal the connector 64. The valve 68 is of known type which actuates by contact of the tip of the syringe. The valve 68 has outer dimensions approximately less than the outer diameter of the shaft 40. As shown, the valve 68 is connected in fluid communication to the proximal end of the inflation lumen 48 by a hollow tubular section 70.

In use, the needle 10 is passed under a radiologic vision until the tip 12 of the needle is located in the renal calyces to obtain access to the kidney chamber. With the needle 10 in place, the guide wire 16 is passed through the needle 10, and the needle is removed with the guide wire 16 in place to establish a path to the kidney K. Next, a plurality of dilators are inserted over the guide wires 16 in order to increase the size of the path to the kidney, and the dilators are then removed.

The stylet 22 is then passed through the connector 64 and drainage lumen 46 of the catheter 38 until the distal end 26 of the stylet 22 contacts the tip 58. The catheter 38 and stylet 22 are then passed over the guide wire 16 with the guide wire 16 extending through the tip opening 60 and through the hollow tube 24 until a distal portion of the catheter 38 is located in the renal calyces. During this time, the stylet 22 facilitates the insertion procedure of the catheter 38 by providing rigidity to the catheter 38. At this time, the tip of the syringe is utilized to contact the valve 68 in order to actuate the valve, and fluid is pumped through the actuated valve 68 and inflation lumen 48 to inflate the sleeve 50 in the renal calyces. Finally, the connector 64 is expanded to receive an adapter at the upstream end of a drainage tube which is connected to a drainage bag, and urine drains from the renal calyces C through the catheter 38 and drainage tube to the drainage bag for retention therein.

The scope 32 is utilized by the physician in the event that he desires to view the inside of the kidney K. In this event, the drainage tube is removed from the connector in order to permit contraction of the connector. Next, the sheath 34 of the scope 32 is passed over the valve 68, the connector 64 and the shaft 40 of the catheter 38. The sleeve 50 of the catheter 38 is then deflated through use of a syringe, and the catheter 38 is removed from the sheath 34. The optic telescope 36 is then inserted through the sheath 34, and the inside of the kidney may be viewed through the telescope 36.

After the viewing has been completed, the telescope 36 is removed from the sheath 34, and the catheter 38 is again inserted through the sheath 34 until the distal portion of the catheter 38 is located in the renal calyces, after which the sleeve 50 is inflated in the renal calyces. Finally, the sheath 34 is removed over the shaft 40, the contacted connector 64, and the valve 68, after which the connector 64 is again attached to the drainage tube.

According to a method of performing a nephrostomy procedure, a path is established through the body of a patient to the renal calyces, and a catheter is inserted through the path with the distal portion of the catheter being located in the renal calyces, after which a sleeve of the catheter is inflated in the renal calyces. A sheath of a scope is then passed over a shaft of the catheter including a connector and an inflation valve of the catheter.

The foregoing detailed description is given for clearness of understanding only, and no unnecessary limitations should be understood therefrom, as modifications will be obvious to those skilled in the art.

I claim:

1. A catheter, comprising:
   an elongated shaft having a drainage lumen; and
   an expansible fluted hollow connector and being closed circumferentially around the connector extending from a proximal end of the shaft, and defining a continuation of the drainage lumen, said connector being at least as small in diameter as the shaft, with the flute defining a portion of the outer surface of the connector.

2. A catheter, comprising:
   an elongated shaft having a drainage lumen extending therethrough, and an inflation lumen extending through a wall of the shaft;
   an elastic sleeve bonded to a distal portion of the shaft in circumferential zones and defining a cavity beneath the sleeve communicating with the inflation lumen;
   a hollow expansible fluted connector extending from a proximal end of the shaft and defining a continuation of the drainage lumen, said connector having outer transverse dimensions approximately less than the outer diameter of the shaft;
   a narrow inflation valve located proximal the connector, said valve having outer transverse dimensions approximately less than the outer diameter of the shaft; and
   means connecting the valve in fluid communication to a proximal end of the inflation lumen.

3. The catheter of claim 2 wherein the connecting means comprises a hollow tubular section extending between the valve and the proximal end of the inflation lumen.

4. A method of performing a nephrostomy procedure with a catheter having a connector and inflation valve and a scope having a sheath, comprising the steps of:
   establishing a path through the body of a patient to the renal calyces;
   inserting a catheter through the path until a distal portion of the catheter is located in the renal calyces;
   inflating a sleeve of the catheter in the renal calyces; and
   passing a sheath of a scope over a shaft of the catheter, said passing step further comprising the step of passing the sheath over a connector and inflation valve of the catheter.

5. The method of claim 4 including the steps of inserting a guide wire through the path, and passing the catheter over the guide wire through a distal opening and drainage lumen of the catheter.

6. The method of claim 4 including the steps of removing the catheter from the sheath, inserting an optic telescope through the sheath, viewing the kidney through the telescope, removing the telescope from the sheath, inserting the catheter through the sheath, and removing the sheath over the catheter.

* * * * *